United States Patent [19]

Nichols et al.

[11] Patent Number: 5,374,282

[45] Date of Patent: Dec. 20, 1994

[54] AUTOMATIC SENSITIVITY ADJUST FOR CARDIAC PACEMAKERS

[75] Inventors: Lucy M. Nichols, Maple Grove; Glenn M. Roline, Anoka; Tom D. Bennett, Shoreview; David L. Thompson, Fridley, all of Minn.

[73] Assignee: Medtronic, Inc., Minneapolis, Minn.

[21] Appl. No.: 786,134

[22] Filed: Oct. 31, 1991

[51] Int. Cl.$^5$ ............................................. A61N 1/365
[52] U.S. Cl. ......................................... 607/18; 607/23; 607/25; 607/28
[58] Field of Search ................. 128/419 PG, 734, 736, 128/667; 607/9, 11, 17, 18, 23, 25, 28

[56] References Cited

U.S. PATENT DOCUMENTS

| | | | |
|---|---|---|---|
| 4,407,296 | 10/1983 | Anderson | 128/675 |
| 4,485,813 | 12/1984 | Anderson et al. | 128/675 |
| 4,556,063 | 12/1985 | Thompson et al. | 128/419 |
| 4,640,285 | 12/1987 | DeCote, Jr. et al. | 128/419 |
| 4,708,144 | 11/1987 | Hamilton et al. | 128/419 |
| 4,766,902 | 8/1988 | Schroeppel | 128/419 |
| 4,768,511 | 9/1988 | DeCote, Jr. | 128/419 |
| 4,827,934 | 5/1989 | Ekwall | 128/419 |
| 4,880,004 | 11/1989 | Baker, Jr. et al. | 128/419 |
| 4,903,699 | 2/1990 | Baker, Jr. et al. | 128/419 |
| 5,081,987 | 1/1992 | Nigam | 128/419 PG |
| 5,127,404 | 7/1992 | Wyborny et al. | 128/419 |
| 5,133,349 | 7/1992 | Heinze | 128/419 PG |
| 5,134,997 | 8/1992 | Bennett et al. | 128/419 PG |
| 5,137,019 | 8/1992 | Pederson et al. | 128/419 PG |

*Primary Examiner*—George Manuel
*Attorney, Agent, or Firm*—Harold R. Patton

[57] ABSTRACT

A pacemaker capable of automatically adjusting the sensitivity of its sense amplifier to electrical cardiac signals is disclosed. In one embodiment, a pacemaker having a pressure sensor disposed on the distal end of its pacing/sensing lead counts the number of pressure events and electrical events which occur during an autosensitivity timing period. If the number of electrical events exceeds the number of pressure events by more than a predetermined margin, the sense amplifier's sensitivity threshold is decreased. If the number of electrical events does not exceed the number of pressure events by more than the predetermined margin, the sense amplifier's sensitivity threshold is increased. In another embodiment, the pacemaker maintains a running average of the peak voltages of sensed electrical events over a predetermined history period. Periodically, the pacemaker computes the ratio of the running average of peak voltages to a preprogrammed sense margin value, and adjusts the sensitivity threshold of the sense amplifier according to this computation. By basing the adjustment of the sense amplifier's sensitivity threshold on a long-term average of peak sense values, the effects of cycle-to-cycle variation in sensed values are minimized. In still another embodiment of the invention, a pressure sensor alone is employed to detect natural cardiac events.

11 Claims, 9 Drawing Sheets

AUTOMATIC SENSITIVITY ADJUST FOR CARDIAC PACEMAKERS

FIELD OF THE INVENTION

This invention relates generally to the field of cardiac pacemakers, and more particularly relates to the sensing of cardiac signals.

BACKGROUND OF THE INVENTION

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricle of the patient's heart, and delivers trial pacing stimuli in the absence of signals indicative of natural trial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiologically-based signals, such as signals from sensors for measuring the pressure inside the patient's ventricle or for measuring the level of the patient's physical activity.

In any pacemaker which delivers stimulating pulses in response to the presence or absence of natural electrical cardiac activity, the sensitivity of the pacemaker to natural cardiac signals is of critical importance. A pacemaker's sense amplifier circuitry must be sensitive enough to ensure detection of cardiac signals, which are typically of relatively low-magnitude (on the order of one to ten millivolts or so), especially in the case of trial sensing. A pacemaker having sense amplifier circuitry that is not sensitive enough might lose synchronization with natural cardiac rhythm, or deliver pacing stimuli at inappropriate times, if all cardiac events are not sensed. This phenomenon is known as "undersensing". At the same time, however, the pacemaker's sense amplifier should not be so sensitive that certain non-electrical cardiac signals, electromagnetic noise, myopotentials, and the like, cause the pacemaker to erroneously "sense" a cardiac event which did not actually occur. Such false sensing, also known as "oversensing", is undesirable since oversensing, like undersensing, can cause the pacemaker to deliver pacing stimuli at inappropriate times, can cause pacing at high rates, can initiate pacemaker-mediated tachycardia (PMT), can cause the pacemaker to lose synchronization with the patient's natural cardiac activity or can totally inhibit pacing.

A pacemaker's ability to sense cardiac signals is typically controllable by means of circuitry for adjusting the sensitivity threshold of the pacemaker's sense amplifier, such that electrical signals resulting from depolarization of the cardiac muscle must exceed this threshold in order for the cardiac event to be recognized. A pacemaker's sensing threshold is typically defined in terms of a minimum voltage level for the input signal, or a minimum time period during which the input signal must exceed a minimum voltage level.

In some pacemakers, the sensitivity threshold of the sense amplifier is preset during manufacture. Other pacemakers have adjustable sensitivity threshold sense amplifiers which must be set by the implanting physician prior to implant. In U.S. Pat. No. 4,640,285 to DeCote, Jr. et al., for example, an external device coupled between a pacemaker to be implanted and the pacemaker's leads is used to establish a sufficient safety margin between the pacemaker's sensing threshold and natural cardiac activity. Once the safety margin has been established, the pacemaker's threshold is programmed accordingly, and the pacemaker is implanted. In still other pacemakers, the sensitivity threshold may be adjusted after implantation by means of an external programming device. With such programmable pacemakers, the pacemaker's response to the patient's natural cardiac activity can be monitored after implantation, such as on an EKG monitor, and the sensitivity adjusted to a desired level.

One complication relating to setting the sensitivity of a pacemaker's sense amplifier is that the strength of cardiac signals received at the sense amplifier's inputs may change over time. Thus, a sensitivity threshold that is appropriate for a patient at the time of implantation might, at some later time, prove to be too high or too low, leading to undersensing or oversensing. Changes in the strength of electrical cardiac signals received by the pacemaker may result from normal or pathological changes in the heart's intrinsic activity, or from so-called "lead maturation" effects, including changes in the positioning of implanted leads, or changes in the conductive properties of the heart muscle in the region surrounding the leads, such as might result from myocardial infarction and fibrotic tissue growth around the lead. Pacemakers in which the sensitivity is adjusted only at the time of manufacture can only compensate for the occurrence of such changes by having a relatively low sensing threshold, so that even weak cardiac signals may be detected. This increases the probability of oversensing, by making the pacemaker prone to false sensing of electrical noise or myopotentials. Pacemakers in which the sensing threshold is adjusted only at the time of manufacture must be explanted and replaced or the sensing lead repositioned in order to compensate for changes in the strength of received electrical signals. Pacemakers which are programmable after implantation with an external programming device are preferable to fixed-sensitivity pacemakers, but a visit to the pacemaker clinic is required. This increases the necessity and frequency of follow-up consultations between the physician and the patient, which can be costly and inconvenient. In addition, transiently occurring changes will often go undetected.

Several attempts in the prior art have been made to cause a pacemaker's sense amplifier threshold to be automatically adjusted and maintained at an appropriate level for a given patient. Such automatic adjustment has the advantage of reducing the likelihood of oversensing, since the threshold need not be set to some low, fixed level, and also reduces the need for follow-up visits to the physician's office. In U.S. Pat. No. 4,766,902 to Schroeppel, for example, there is disclosed a pacemaker having two separate sense amplifiers. One of the sense amplifiers has a slightly lower sensing threshold, and thus a slightly higher sensitivity level, than the other. The thresholds of the two sense amplifiers are automatically adjusted so that the more sensitive sense amplifier will sense cardiac activity but the less sensitive one will not.

Similarly, in U.S. Pat. No. 4,768,511 to DeCote, there is disclosed a pacemaker having a single, fixed-gain sense amplifier. The output of the sense amplifier is coupled to a pair of voltage comparators, one of which has a slightly lower threshold than the other. The thresholds of the two voltage comparators are automatically adjusted so that one of the voltage comparators will respond to the output of the sense amplifier while the other one will not.

Another technique which has been proposed in the prior art to provide for the automatic adjustment of a pacemaker's sensitivity is disclosed in U.S. Pat. No. 4,708,144 to Hamilton et al. According to this patent, the pacemaker measures the peak value of each detected intrinsic ventricular event, and adjusts the pacemaker's sensitivity according to a long-term average of these values.

In U.S. Pat. Nos. 4,903,699 and 4,880,004 to Baker, Jr. et al. there is disclosed a pacemaker sense amplifier having automatic gain control (AGC). The sense amplifier sets a sense threshold and a slightly higher AGC threshold, such that a cardiac event which exceeds the sense threshold but not the AGC threshold indicates that the gain of the amplifier should be increased, while a cardiac event which exceeds both the sense and AGC thresholds indicates that the gain of the amplifier should be decreased.

In U.S. Pat. No. 4,827,934 to Ekwall there is disclosed a sensitivity adjustment scheme in which the amount of time during which the cardiac signal exceeds a preset threshold is used to determine whether the sensitivity of the sense amplifier should be increased or decreased.

In each of the aforementioned techniques in the prior art for providing automatic adjustment and/or maintenance of the sensitivity of a pacemaker, the determination whether to increase or decrease the sensitivity is made based on some analysis of electrical cardiac activity detected by the sense amplifier. One disadvantage of such techniques is that if no electrical activity is sensed, no determination of the appropriate sensitivity level can be made. In addition, techniques based solely on analysis of sensed electrical cardiac activity are susceptible to problems arising from extraneous electrical signals which may be present, such as myopotentials or electromagnetic interference from external sources.

Another disadvantage of prior techniques for automatic adjustment of sensitivity thresholds in pacemakers arises from the prior techniques' failure to account for natural beat-to-beat variations in the magnitude of sensed electrical cardiac signals. That is, prior threshold adjustment schemes cannot distinguish between changes in peak sense levels that result from some form of lead maturation or chronic changes in intrinsic cardiac activity (i.e., changes which require adjustment of the sensitivity), and changes in peak sense levels that result from natural variation in intrinsic electrical cardiac activity (which do not require adjustment of the sensitivity).

It is accordingly a feature of the present invention that a scheme for automatically adjusting the sensitivity of a pacemaker sense amplifier is provided.

It is another feature of the present invention that adjustment of the pacemaker's sensitivity threshold is made based on true changes in sensed electrical cardiac signals, rather than on normal beat-to-beat variations in sensed electrical cardiac signals.

Another feature of the present invention is that effects of extraneous electrical signals such as external electromagnetic interference, myopotentials, and the like, on the adjustment of the pacemaker's sensitivity threshold, are minimized.

SUMMARY OF THE INVENTION

According to the present invention, a cardiac pacemaker is provided in which the sensitivity threshold setting of the pacemaker's sense amplifier is automatically adjusted and optimized to the patient's spontaneous electrical cardiac activity. In one embodiment of the invention, the threshold setting of the sense amplifier is determined based upon a comparison of sensed electrical cardiac activity with a pressure signal from a right-ventricle indwelling pressure sensor representative of mechanical contraction of the heart muscle during intrinsic or paced events. Such a pressure signal is not typically affected by myopotentials or electromagnetic interference, and thus provides a more consistent basis for determination of the sensitivity threshold than would the electrical cardiac signal alone. According to the present invention, the electrical cardiac signal and pressure signal are periodically or continuously monitored and compared during sensed events, allowing the sensing threshold to be adjusted to prevent both oversensing and undersensing. The time period between successive readjustments of the sensitivity threshold is long enough to include many cardiac cycles, so that the effects of normal beat-to-beat variations in sensed electrical cardiac activity on the sensitivity threshold are minimized.

In another embodiment of the invention, the determination of an appropriate sensitivity threshold is periodically and automatically made based upon a long-term averaging of prior sensed electrical cardiac activity, such that the effects of ordinary beat-to-beat variations in cardiac activity on the sensitivity threshold are minimized.

BRIEF DESCRIPTION OF THE DRAWINGS

The foregoing and other features of the present invention will be best appreciated with reference to the detailed description of a specific embodiment of the invention, which follows, read in conjunction with accompanying drawings, wherein.

DETAILED DESCRIPTION OF SPECIFIC EMBODIMENTS OF THE INVENTION

Figure 1:
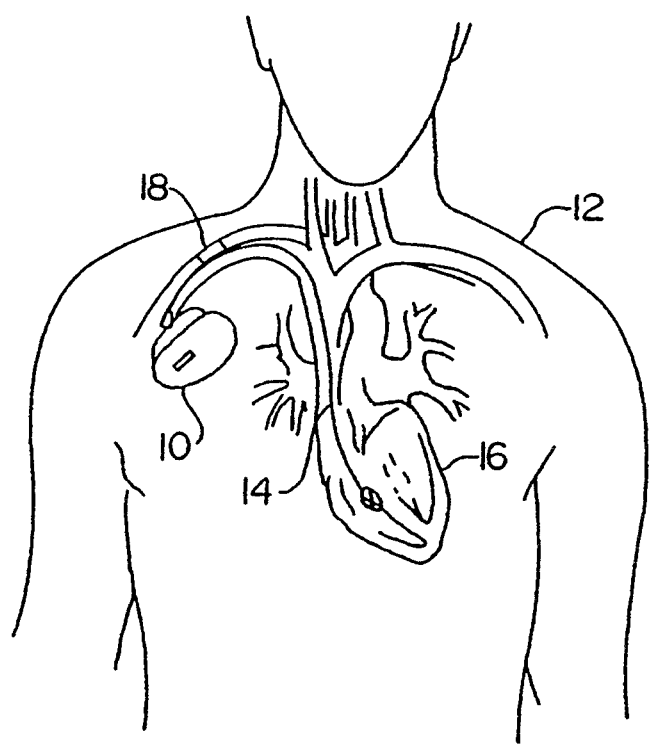
FIG. 1 is a diagram showing a the placement in a patient of a pacemaker in accordance with the present invention.

FIG. 1 shows generally how a pacemaker 10 in accordance with the present invention may be implanted in a patient 12. A pacemaker lead 14 is electrically coupled to pacemaker 10 and extends into the patient's heart 16 via a vein 18. The distal end of lead 14 includes one or more exposed conductive electrodes for receiving electrical cardiac signals and for delivering electrical pacing stimuli to the patient's heart 16. In accordance with one embodiment of the invention to be hereinafter described, the distal end of pacemaker lead 14 may also incorporate a pressure transducer (not shown in FIG. 1 due to the small scale of that Figure) for producing electrical signals representative of the pressure inside heart 16.

Figure 2:
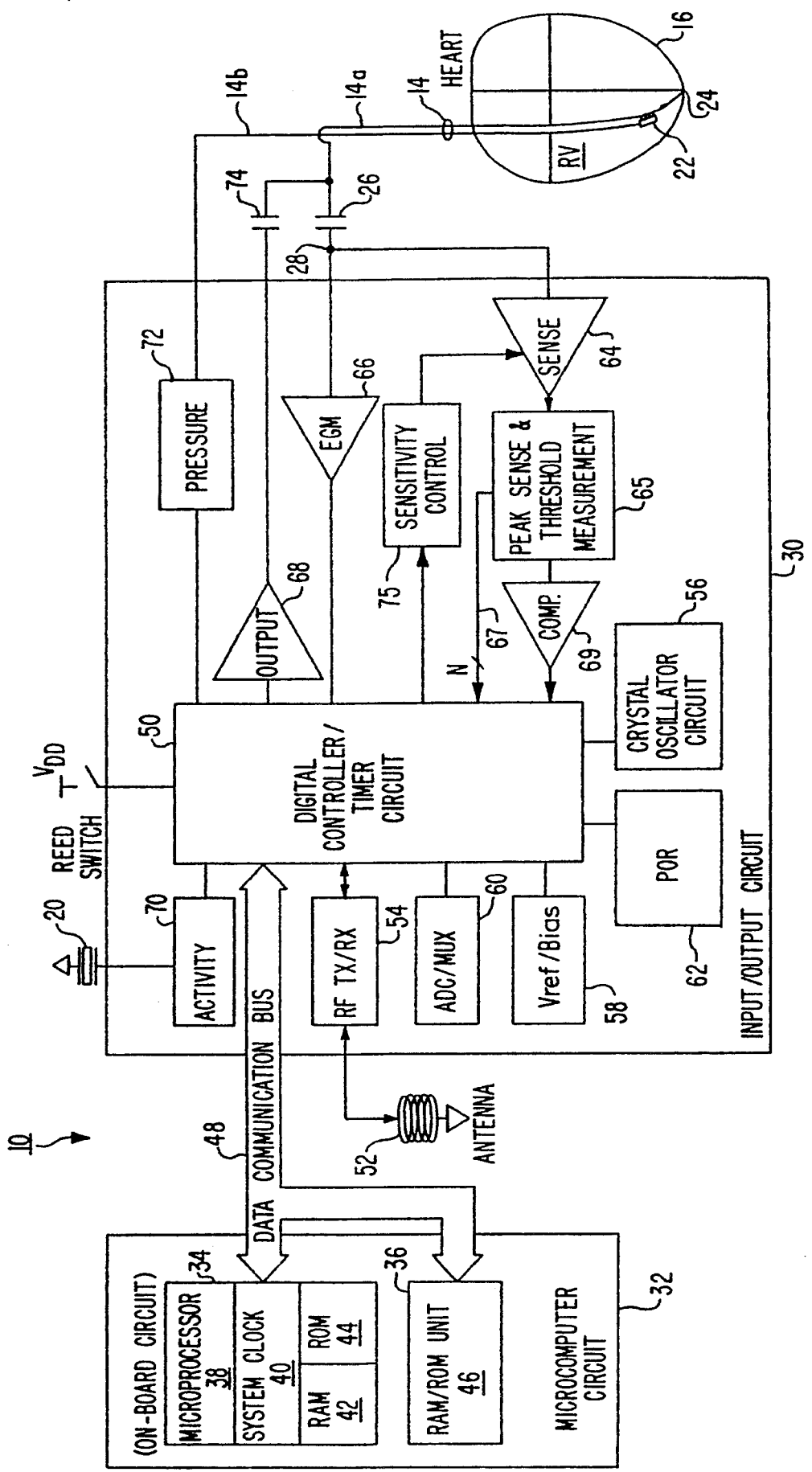
FIG. 2 is a block diagram of the circuitry of a pacemaker in accordance with one embodiment of the present invention.

Turning to FIG. 2, a block diagram of pacemaker 10 from FIG. 1 is shown. Although the present invention is described in conjunction with a pacemaker 10 having a microprocessor-based architecture, it will be understood that it could be implemented in any logic based, custom integrated circuit architecture, if desired. It will also be understood that the present invention may be utilized in conjunction with other implantable medical devices, such as cardioverters, defibrillators, neural stimulators, cardiac assist systems, and the like.

In the embodiment shown in FIG. 1, pacemaker 10 includes an activity sensor 20, which may be, for example, a piezoelectric element bonded to the inside of the pacemaker's housing. Sensor 20 provides a sensor output which varies as a function of a measured parameter that relates to the metabolic requirements of patient 12. In addition, pacemaker 10 includes a pressure sensor 22 disposed at the distal end of lead 14, as previously noted, which may be similarly used to ascertain the metabolic requirements and/or cardiac output of patient 12. Pressure sensor 22 may be a piezoelectric element such as is disclosed in U.S. Pat. No. 4,407,296 to Anderson, entitled "Integral Hermetic Implantable Pressure Transducer", or U.S. Pat. No. 4,485,813 to Anderson et al., entitled "Implantable Dynamic Pressure Transducer System", each assigned to the assignee of the present invention and incorporated herein by reference.

Pacemaker 10 is schematically shown in FIG. 2 to be electrically coupled via a pacing lead 14 to a patient's heart 16. Lead 14 includes an intracardiac electrode 24 and pressure sensor 22 located near its distal end and positioned within the right ventricular (RV) chamber of heart 16. Lead 14 can carry either unipolar or bipolar electrodes as is well known in the art. In the presently disclosed embodiment, lead 14 which couples pacemaker 10 to the ventricular endocardium can comprise a steroid-tipped, unipolar lead with an integral pressure transducer of the type described in the aforementioned references. Electrode 24 is coupled via suitable lead conductor 14a through input capacitor 26 to node 28 and to input/output terminals of an input/output circuit 30. Output from first sensor 20 is coupled to input/output circuit 30. Output from pressure sensor 22 is also coupled to input/output circuit 30 via suitable lead conductor 14b.

Input/output circuit 30 contains the analog circuits for interface to the heart 16, first sensor 20, pressure sensor 22, and antenna 52, as well as for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. Off-board circuit 36 includes an off-board RAM/ROM unit 46. Microcomputer circuit 32 is coupled by data communication bus 48 to a digital controller/timer circuit 50. Microcomputer circuit 32 may be fabricated of custom integrated circuit devices augmented by standard RAM/ROM components.

It will be understood that the electrical components represented in FIG. 2 are powered by an appropriate implantable battery power source, not shown, in accordance with common practice in the art.

An antenna 52 is connected to input/output circuit 30 for purposes of uplink/downlink telemetry through RF transmitter/receiver (RF TX/RX) unit 54. Telemetering both analog and digital data between antenna 52 and an external device, such as an external programmer (not shown), is accomplished in the presently disclosed embodiment by means of all data first being digitally encoded and then pulse-position modulated on a damped RF carrier, as substantially described in co-pending U.S. patent application Ser. No. 468,407, filed on Jan. 22, 1990, entitled "Improved Telemetry Format", which is assigned to the assignee of the present invention and which is incorporated herein by reference.

A crystal oscillator circuit 56, typically a 32,768-Hz crystal-controlled oscillator, provides main timing clock signals to digital controller/timer circuit 50. A Vref/Bias circuit 58 generates stable voltage reference and bias currents for the analog circuits of input/output circuit 30. An analog-to-digital converter/multiplexor (ADC/MUX) unit 60 digitizes analog signals and voltages to provide "real-time" telemetry of pressure and intra cardiac signals and battery end-of-life (EOL) replacement function. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input/output circuit 30.

Digital controller/timer circuit 50 is coupled to a sense amplifier 64 and an electrogram amplifier 66 for receiving amplified and processed signals picked up from electrode 24 through lead conductor 14a and capacitor 26 representative of the electrical activity of the patient's heart 16. Sense amplifier 64 amplifies sensed electrical cardiac signals and provides this amplified signal to peak sense and threshold measurement circuitry 65, which provides an indication of peak sensed voltages and the measured sense amplifier threshold voltage on multiple conductor signal path 67 to digital controller/timer circuit 50. The amplified sense amplifier signal is also provided to a comparator 69. The electrogram signal developed by EGM amplifier 66 is used in those occasions when the implanted device is being interrogated by an external programmer, not shown, in order to transmit by uplink telemetry a representation of the analog electrogram of the patient's electrical heart activity as described in U.S. Pat. No. 4,556,063, issued to Thompson et al., assigned to the assignee of the present invention and incorporated herein by reference. An output pulse generator 68 provides the pacing stimulus to the patient's heart 16 through coupling capacitor 74 in response to a pacing trigger signal developed by digital controller/timer circuit 50 each time the escape interval times out, or an externally transmitted pacing command has been received, or in response to other stored commands as is well known in the pacing art.

Digital controller/timer circuit 50 is coupled to an activity circuit 70 for receiving, processing, and amplifying signals received from activity sensor 20. Activity circuit 70 produces an activity signal which is representative of the patient's metabolic requirements. Similarly, digital controller/timer circuit 50 is coupled to a pressure circuit 72 for receiving, amplifying and processing sensor output from pressure sensor 22. In the presently disclosed embodiment of the invention, pressure circuit 72 produces an amplified, filtered analog pressure signal which is received by digital controller/timer circuit 50. In conjunction with ADC/MUX 60, digital controller/timer circuit samples and digitizes the pressure signal from pressure circuit 72 to obtain a digital representation of the peak value of intracardiac pressure during each cardiac cycle. This value is provided to microprocessor 34, which maintains a running average over a previous number of cardiac cycles (e.g. sixteen) of the intracardiac pulse pressure. In addition, for each pressure value received from digital controller/timer circuit 50, microprocessor 34 determines whether the pressure value exceeds a certain pressure threshold value. In the presently disclosed embodiment of the invention, the pressure threshold value is determined as a percentage of the aforementioned running average of pressure values. This percentage may be in the range from 25% to 75%, and it is contemplated by the inventors that a threshold value of approximately 37½% of the running average will be a typical threshold setting.

When microprocessor 34 determines that a pressure value received from digital controller/microprocessor circuit 50 exceeds the pressure threshold value, this is interpreted as a "true" pressure beat, i.e., a pressure beat that corresponds to a cardiac contraction. If a pressure value is received by microprocessor 34 that is found not to exceed the pressure threshold value, this is interpreted as a "false" pressure beat which does not correspond to a cardiac contraction.

With continued reference to FIG. 2, input/output circuit 30 further includes sensitivity control circuitry 75 coupled between digital controller/timer circuit 50 and sense amplifier circuit 64. Sensitivity control circuit 75 controls the sense amplifier gain and thus the sensing threshold of sense amplifier 64 as instructed by digital controller/timer circuit 50. Digital controller/timer circuit 50 provides the appropriate information to microcomputer circuit 32 which determines whether the sensitivity threshold of sense amplifier 64 needs to be increased or decreased based on an analysis of input signals from pressure circuit 72 and sense amplifier 64. This analysis of input signals shall be hereinafter described in greater detail with reference to FIGS. 3 and 4.

As previously noted, digital controller/timer circuit 50 maintains various digital timers and counters for establishing certain timing windows associated with the operation of peripheral components within input/output circuit 30. One of the timers maintained in digital controller/timer circuit 50 is an AUTOSENSE timer which establishes a predetermined rate (the AUTOSENSE INTERVAL) at which the sensitivity of sense amplifier 64 is periodically adjusted. A SENSE COUNT count value is maintained in RAM 42 under control of microcomputer 32; the SENSE COUNT value corresponds to a running count of sensed events (i.e. electrical cardiac events which exceed the sensitivity threshold of sense amplifier 64) which have occurred during the current AUTOSENSE interval. Similarly, a PULSE PRESSURE COUNT count value is maintained in RAM 42 by microcomputer 32, the PULSE PRESSURE COUNT value corresponding to a running count of the number of "true" pressure beats which have occurred during the current AUTOSENSE interval.

Figure 3:
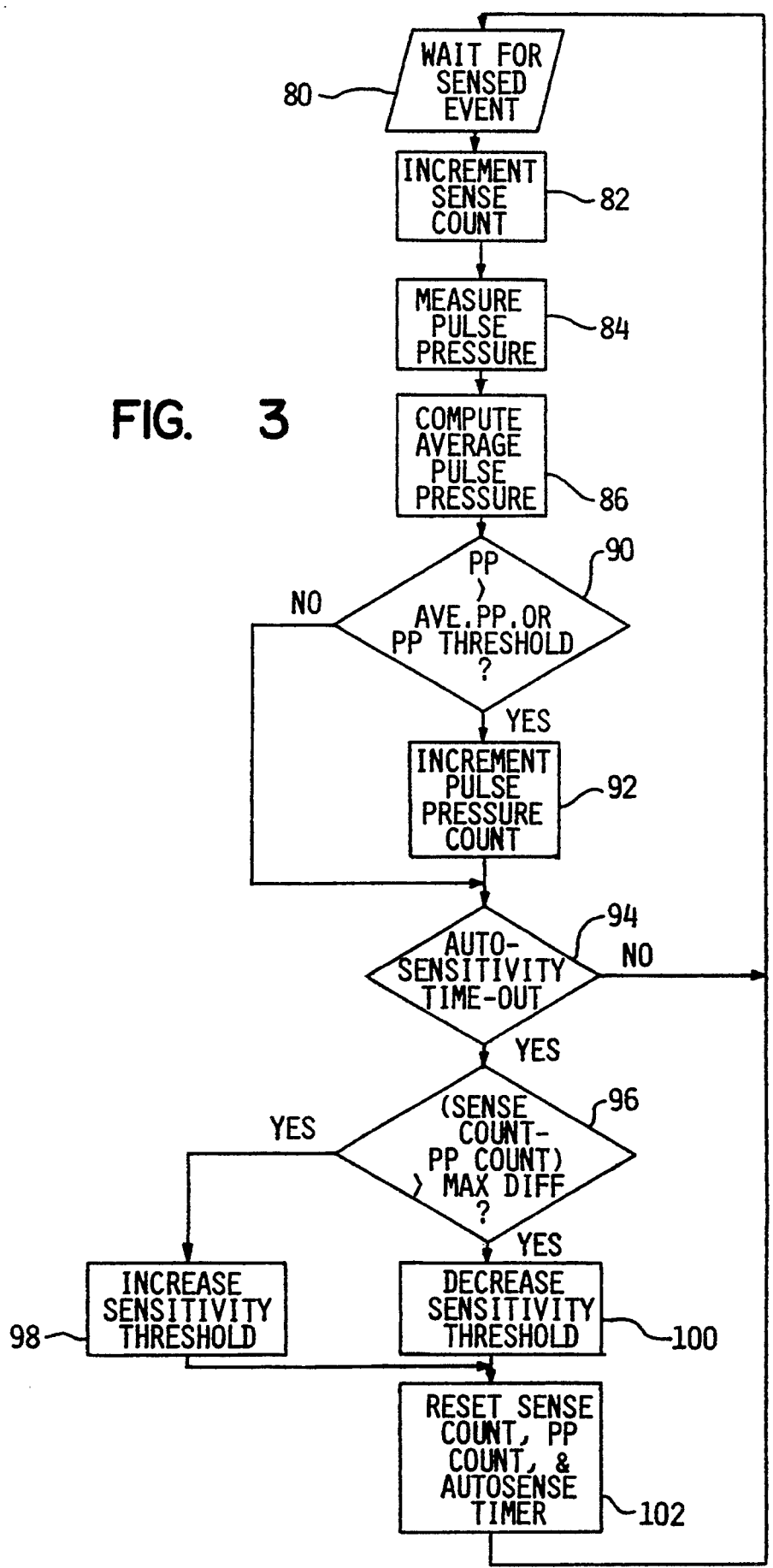
FIG. 3 is a flow diagram illustrating a mode of operation of the pacemaker of FIG. 2.

Turning now to FIG. 3, a flow diagram is shown which illustrates an automatic sensitivity adjusting algorithm in accordance with the presently disclosed embodiment of the invention. The algorithm of FIG. 3 begins upon the sensing of a cardiac event, as represented by block 80. Upon sensing a cardiac event, digital controller/timer circuit increments the value of its aforementioned internal SENSE COUNT counter. This step is represented by block 82. Next, digital controller/timer circuit instructs pressure circuit 72 to activate pressure sensor 22 and take a reading of the RV pressure, as represented in FIG. 3 by block 84. It is contemplated by the inventors that a measure of the peak pulse pressure for a given sensed cardiac event can be obtained by taking a reading of the pulse pressure within a 200-mSec window following the sensing of that cardiac event.

In block 86, microcomputer 32 computes a running average of the RV pressure over the previous 16 sensed events.

Next, in decision block 90, a determination is made whether the pulse pressure measured in block 84 exceeded the predetermined pressure threshold value. As previously noted with reference to FIG. 2, this determination is based on whether a peak in the analog pressure waveform from pressure circuit 72 exceeds a certain percentage of a running average of previous pressure values. If so, the aforementioned PULSE PRESSURE COUNT value is incremented, as represented by block 92; otherwise, the PULSE PRESSURE COUNT value is not incremented, and the algorithm proceeds directly to block 94. In the pacemaker of FIG. 2, the determination whether the measured pulse pressure exceeded the predetermined threshold value is made by microcomputer 32; if the measured pressure did exceed the threshold value, the PULSE PRESSURE COUNT value is incremented.

In block 94 of FIG. 3, microcomputer 32 determines whether an AUTOSENSE timer time-out has occurred. In the presently disclosed embodiment of the invention, it is contemplated that an AUTOSENSE timeout will occur approximately every 24-hours, although AUTOSENSE timeout periods of any duration, from one cardiac cycle to a month, may be employed. If an AUTOSENSE timeout has not occurred, flow returns from block 94 to block 80 wherein input/output circuit 30 waits for another sensed event to occur. If an AUTOSENSE timeout has occurred, flow proceeds to decision block 96.

In block 96, microcomputer 32 compares the difference between the values in the SENSE COUNT and PULSE PRESSURE COUNT counters to determine whether these two values differ by more than a predetermined percentage value, MAX DIFF. The percentage difference between the SENSE COUNT and PULSE PRESSURE COUNT values reflects the number of sensed electrical events during the previous AUTOSENSE interval which were not accompanied by a peak pressure corresponding to an actual cardiac cycle. That is, if the percentage difference between the two counter values is too great, this suggests that the sense amplifier is responding to electrical signals which are not actual cardiac signals, but possibly myopotentials, electromagnetic interference or the like. Thus, if the difference between the two counter values is too great, i.e. the percentage difference exceeds the predetermined percentage value MAX DIFF, the sensitivity threshold of the sense amplifier should be increased, as represented by block 98. When the sensitivity threshold is increased, non-cardiac electrical signals are less likely to exceed the threshold; thus during the next AUTOSENSE interval, the percentage difference between the SENSE COUNT and PULSE PRESSURE COUNT values should decrease, as an indication that only true cardiac events exceed the sensitivity threshold. In this way, oversensing can be avoided. In the presently disclosed embodiment of the invention, it is contemplated that an appropriate value for MAX DIFF is ten percent. The MAX DIFF value may be one of the programmable parameters of pacemaker 10.

If, however, the percentage difference between the SENSE COUNT and PULSE PRESSURE COUNT values in decision block 96 does not exceed MAX DIFF (or if, in fact, the two count values are equal), this can suggest one of two possible conditions: either the sense amplifier sensitivity threshold is set correctly, or it is set too high, so that undersensing is occurring. Since, in accordance with the presently disclosed embodiment of the invention, pressure values are only measured after a sensed electrical event, appropriate sensing cannot be distinguished from undersensing. It is presently believed that the preferred manner of practicing the present invention is to assume that if the sense amplifier is not oversensing, it is undersensing. Therefore, if the percentage difference between the two count values in block 96 does not exceed MAX DIFF, the sensitivity threshold is decreased, as represented in block 100. This has the effect of making the sense amplifier more sensitive to electrical signals. If, upon expiration of subsequent AUTOSENSE intervals, it is determined that the increase in sensitivity occurring in block 100 is leading to oversensing, this will be reflected in the computed percentage difference between the two counter values in block 96, and the sensitivity will again be decreased in block 98.

After the sense amplifier sensitivity threshold is adjusted upward in block 98 or downward in block 100, the AUTOSENSE timer, SENSE COUNT counter, and PULSE PRESSURE COUNT counter are each reset, as represented in block 102, and the entire process is repeated, starting at block 30. The sensitivity threshold will thus oscillate about a threshold that will alternately cause normal sensing and oversensing. Since the process of FIG. 3 is based upon the presumption that if the sense amplifier is not oversensing then it is undersensing, the process of FIG. 3 does not allow for the possibility that the appropriate sensitivity threshold is programmed, and the sensitivity threshold will be adjusted either up or down each time the process is repeated. When an appropriate sensitivity threshold is programmed, therefore, this can result in unnecessary adjustment of the sensitivity threshold, as it oscillates around the appropriate level.

Figure 4:
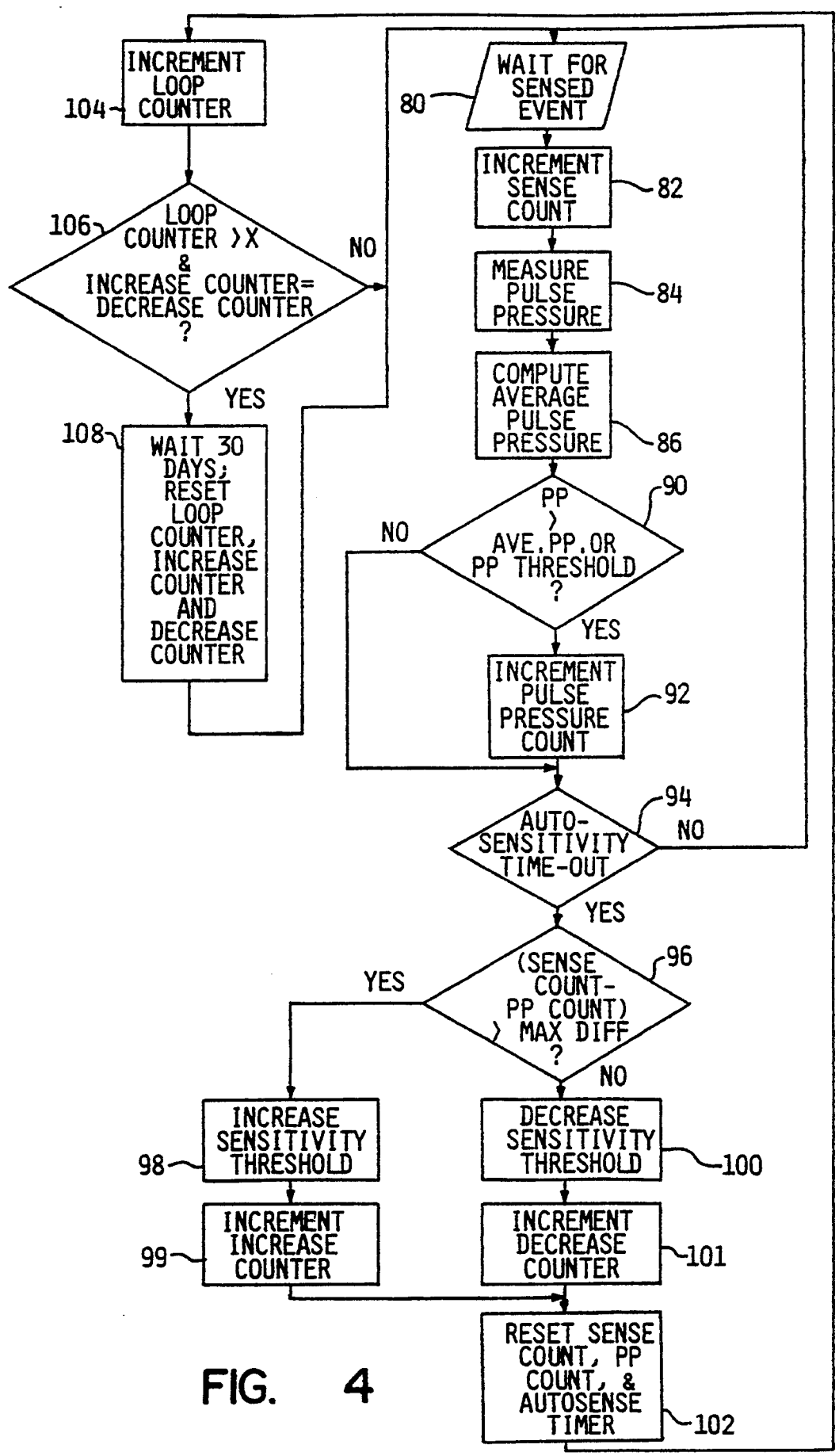
FIG. 4 is a flow diagram illustrating an alternative mode of operation of the pacemaker of FIG. 2.

In order to reduce the amount of unnecessary adjustment of the sensitivity threshold, therefore, a slight modification to the process of FIG. 3 is contemplated, and is depicted in FIG. 4. In FIG. 4, the process steps which are the same as those of FIG. 3 have retained identical reference numerals. The algorithm represented by FIG. 4 differs from that of FIG. 3 only in the utilization of several count values, maintained in an INCREASE COUNTER, a DECREASE COUNTER, and a LOOP COUNTER. The INCREASE COUNTER counts the number of times the sensitivity threshold is increased, while the DECREASE COUNTER counts the number of times the sensitivity threshold is decreased. The LOOP COUNTER counts the number of AUTOSENSE intervals that have occurred. It should be noted that the LOOP COUNTER value will always equal the sum of the INCREASE COUNTER value and DECREASE COUNTER value, since each time an AUTOSENSE time-out occurs, the sensitivity threshold will either be increased or decreased.

In the algorithm depicted in FIG. 4, the steps represented by blocks 80 through 94 are carried out in the same manner as in the algorithm of FIG. 3. From block 94, if an AUTOSENSE time-out has not occurred, flow returns to block 80, as in the algorithm of FIG. 3. If an AUTOSENSE interval has occurred, the comparison in block 96 is made, and the sensitivity threshold is either increased or decreased, in blocks 98 and 100. When the sensitivity threshold is increased, the INCREASE COUNTER value is incremented, as represented by block 99, and if the sensitivity threshold is decreased, the DECREASE COUNTER value is incremented, as represented by block 101. Thereafter, the SENSE COUNT, PULSE PRESSURE COUNT, and AUTOSENSE timers are reset, in block 102. Rather than returning to block 80, however, as in the algorithm of FIG. 3, flow proceeds to block 104, where the LOOP COUNTER value is incremented. In decision block 106, a determination is made whether the LOOP COUNTER value exceeds a predetermined number, X, which may be, for example, ten. If the LOOP COUNTER value does not exceed X, this means that the sensitivity threshold has not been adjusted more than X times, and may not have had sufficient time to arrive at an appropriate level. In this case, flow returns to block 80.

If, however, at block 96, the LOOP COUNTER value exceeds X, and if the INCREASE COUNTER value is equal to the DECREASE COUNTER value, this is taken as an indication that the sensitivity threshold is, as a result of the autosensitivity adjustment, oscillating around an appropriate sensitivity level, as previously described. In this case, therefore, so that continued and unnecessary re-adjustment of the sensitivity setting can be minimized, the autosensitivity adjustment process is temporarily halted, for period of 30 days or so, as represented by block 108. It is to be understood that the 30-day waiting period depicted in FIG. 4 is used for illustrative purposes only, and a different length of time may be deemed appropriate in a particular implementation. In addition, the length of the waiting period of block 108 may be one of the externally programmable parameters of the pacemaker, so that it could be adjusted by an attending physician post-implant by means of the telemetry system previously discussed.

Also in block 108, the INCREASE COUNTER, DECREASE COUNTER, and LOOP COUNTER values are reset to zero. After the waiting period introduced by block 108 has elapsed, the autosensitivity adjustment process is restarted, beginning with block 80.

Figure 5:
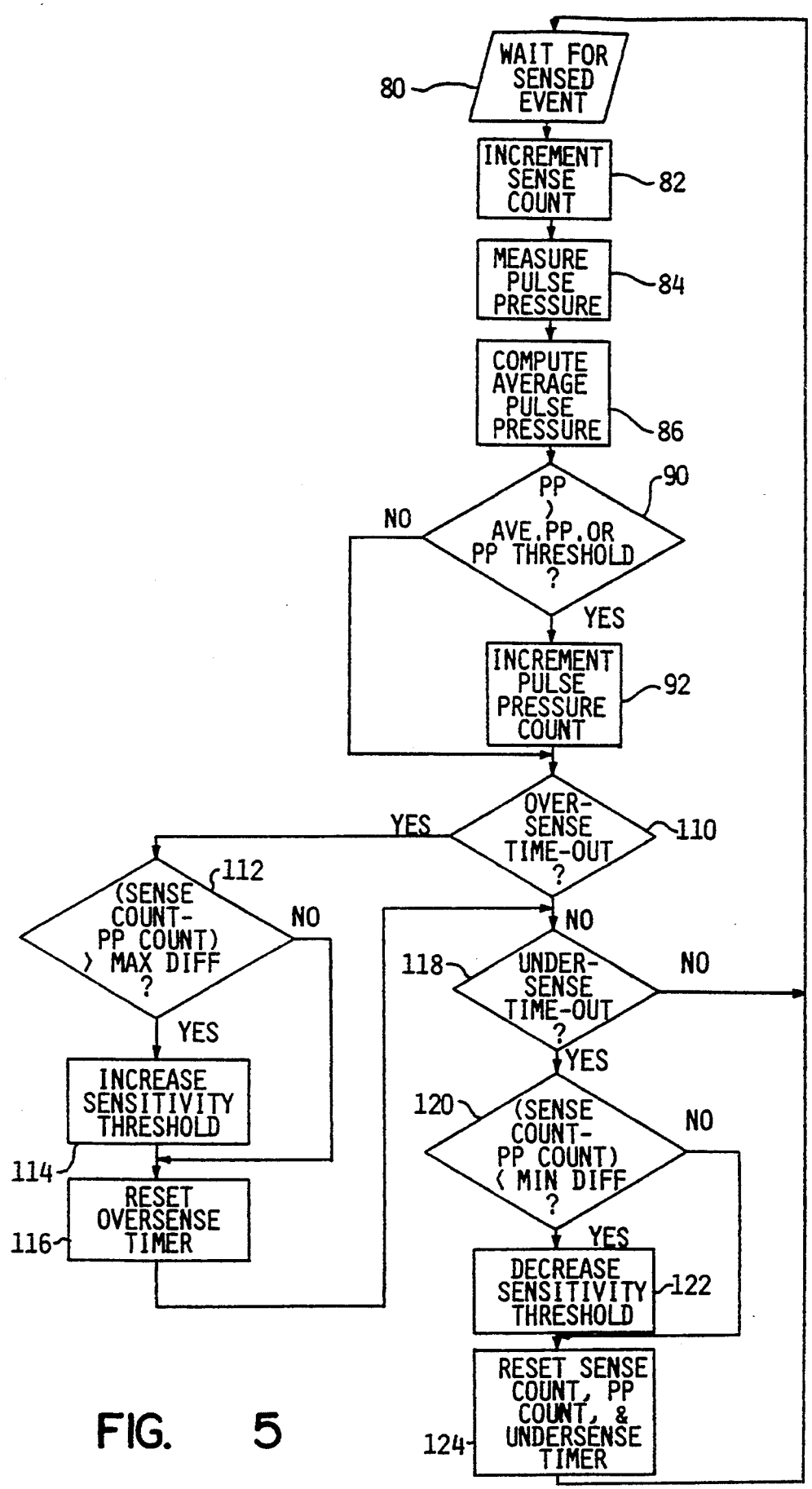
FIG. 5 is a flow diagram illustrating an alternative mode of operation of the pacemaker of FIG. 2.

As previously noted, distinguishing between appropriate sensing and undersensing is not possible when pressure readings are taken only following sensed electrical events. It is contemplated that one way to compensate for this would be to check for oversensing more frequently than undersensing. In FIG. 5, a flow diagram of depicting another modification to the sensitivity adjustment algorithm of FIG. 3 is shown, in which the preliminary steps represented by blocks 80, 82, 84, 86, 90, and 92 are identical to those in the algorithm depicted in FIG. 3, and which have therefore retained identical reference numerals in FIG. 5.

According to the modified algorithm of FIG. 5, two separate timers, an OVERSENSE timer and an UNDERSENSE timer, are utilized, with the OVERSENSE timer defining a shorter time interval than the UNDERSENSE timer. In addition to the MAX DIFF value, a second predetermined value, MIN DIFF, is preset to be the minimum difference between the SENSE COUNT value and the PULSE PRESSURE COUNT values below which undersensing is assumed to have occurred.

After block 92 in FIG. 5, microcomputer 32 will determine whether an OVERSENSE timeout has occurred, as represented in block 110. If an OVERSENSE timeout has occurred, flow proceeds to decision block 112, wherein a determination is made whether the difference between the current SENSE COUNT value and PULSE PRESSURE COUNT value is greater than the predetermined MAX DIFF percentage value. If so, as in the embodiment of FIG. 3, microcomputer 32 instructs sensitivity control circuit 75 to increase the sensitivity threshold of sense amplifier 64, as represented in block 114, thereby making sense amplifier 64 less likely to register a sensed event when no cardiac event has occurred. After increasing the sensitivity threshold, the OVERSENSE timer is reset, in block 116. Thereafter, flow proceeds to block 118. Flow also proceeds to block 118 from decision block 110 if an OVERSENSE timeout has not occurred.

In block 118, a determination is made whether an UNDERSENSE timeout has occurred. If not, flow returns to block 80, where input/output circuit 30 waits for another sensed event. If an UNDERSENSE timeout has occurred in block 118, however, microcomputer 32 compares the difference between the SENSE COUNT and PULSE PRESSURE COUNT values, as represented in block 120. If this difference is less than the predetermined MIN DIFF value, this suggests that either appropriate sensing, or undersensing is occurring. Thus, the sensitivity threshold of sense amplifier 64 is decreased, at block 122. If the difference is greater than MIN DIFF, however, flow proceeds directly to block 124, wherein the SENSE COUNT and PULSE PRESSURE COUNT counters are reset, along with the UNDERSENSE timer. From block 124, flow returns back to block 80, wherein input/output circuit 30 waits for another event to be sensed.

It is to be understood that the modifications to the algorithm of FIG. 3 that are shown in both FIGS. 4 and 5 may be combined in a single embodiment, wherein oversensing is checked for more frequently than undersensing (as in the algorithm of FIG. 5), and wherein once an appropriate sensitivity level is determined, the autosensitivity process is temporarily disabled in order to minimize unnecessary readjustment of the sensitivity level (as in the algorithm of FIG. 4).

Figure 6:
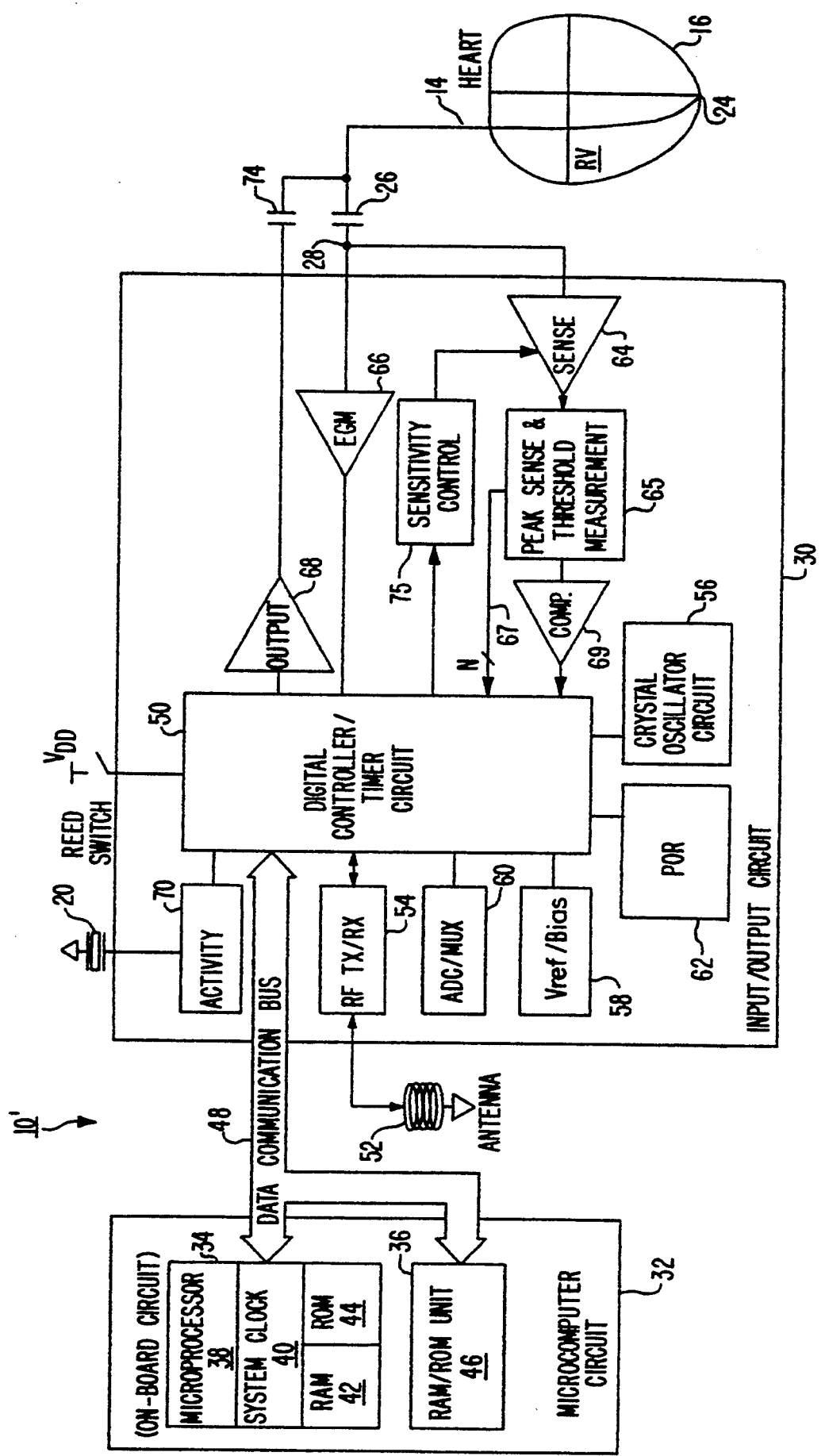
FIG. 6 is a block diagram of the circuitry of a pacemaker in accordance with a second embodiment of the present invention.

Turning now to FIG. 6, a block diagram of a pacemaker 10' in accordance with another embodiment of the present invention is shown, wherein components which are identical to those in pacemaker 10 of FIG. 2 have retained identical reference numerals. In the embodiment of FIG. 6, pacemaker 10' does not necessarily include a pressure sensor or its associated circuitry, these components being omitted from the diagram of FIG. 6. The automatic sensitivity adjustment algorithm employed by pacemaker 10' is based on analysis of sensed electrical cardiac signals, as shall be hereinafter described.

In particular, the sensitivity adjustment algorithm employed by pacemaker 10' is based on a periodic determination of an average peak, filtered, rectified voltage applied to the amplifier threshold detector. This value may be used to optimally adjust the Sense Amplifier Threshold Setting (SATS). Specifically, the SATS value is computed according to the following formula:

$$SATS = \left[ \left( \frac{APSV}{SATM} \right) \times \left( \frac{100}{PSM + 100} \right) \times (CTS + 1) \right] - 1$$

where
SATS=Sense Amplifier Threshold Setting
APSV=Average Peak Sense Value
PSM=Percent Safety Margin
SATM=Sense Amplifier Threshold Measurement
CTS=Current Threshold Setting It is contemplated by the inventors that the SATS value may be calculated on each cardiac cycle. However, because calculation of the SATS value involves operation of microprocessor 38 and hence consumes battery power, such frequent calculation of the SATS value may cause unacceptably high current drain in the implanted device. Instead of calculating the SATS value on each cardiac cycle, therefore, it may be preferable to calculated it only every N cycles, where N is some number of cardiac cycles greater than or equal to 2.

In order to periodically compute the SATS value, pacemaker 10' in accordance with the presently disclosed embodiment of the invention maintains a long-term average, for example over a period of an hour or more, of peak voltages sensed during that period. This long-term average, computed under control of microprocessor 38, can be generated by a standard R/C time constant, a switch capacitor equivalent, or alternatively by a fixed-precision, single-word, cumulative averaging algorithm implemented in microprocessor 38, such as is disclosed by Cloutier and Friedman in "Precision Averaging for Real-Time Analysis" *Communications of the ACM*, July 1983, vol. 26, no. 7, which article is hereby incorporated by reference.

Figure 7:
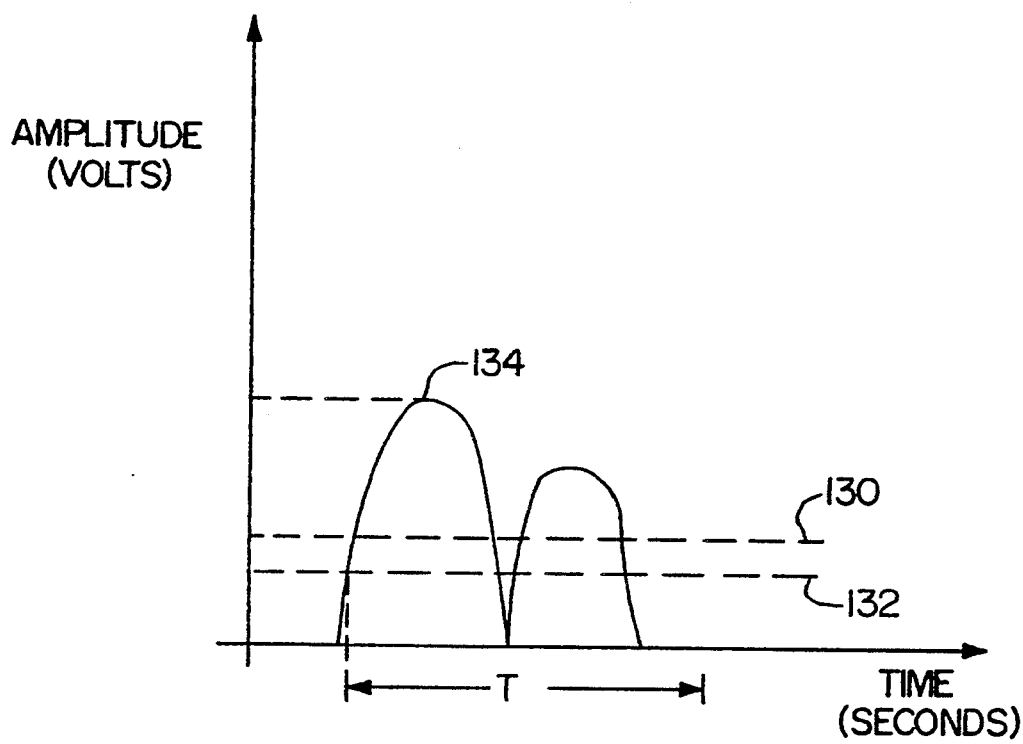
FIG. 7 is an illustration of an electrical signal applied to the sense amplifier comparator of the pacemaker of FIG. 5.

In accordance with the presently disclosed embodiment of the invention, the peak voltage of a sensed signal is determined by observing the sensed signal during an SATS time window of duration T which is initiated upon the sensed signal reaching the programmed threshold value. Referring to FIG. 7, the interval denoted as T along the time axis represents the SATS window. It is contemplated by the inventors that an SATS interval of 110-milliseconds is appropriate for ascertaining the peak value of a sensed cardiac event. In FIG. 7, the programmed sensitivity threshold is denoted by dashed line 130. A typical value for the programmed sensitivity threshold at the input of Input-/Output circuit 30 is 2.5-millivolts. Due to normal component variation, manufacturing process variation, and battery depletion condition, however, the actual sensitivity threshold of sense amplifier 64 may deviate from the programmed value by as much as ±20%. Thus, the actual sensitivity threshold of sense amplifier 64 is represented by dashed line 132. Due to such component variation, accurate computation of the SATS values requires that the actual, rather than programmed, sensitivity threshold be provided to microcomputer 32.

When an electrical signal exceeds the threshold of the sense amplifier, the actual threshold value can be determined by peak sense and threshold measurement circuit 65, and communicated via digital controller/timer circuit 50 to microcomputer 32 via bus 48. As soon as a signal is sensed, SATS window T is initiated, the peak value of the sensed signal during this window being similarly provided to microprocessor 38. In FIG. 7, the peak value is denoted as 134.

Once microprocessor 32 is provided with digital values corresponding to the actual sensitivity threshold and the peak sense value, a SATS value can be calculated. Microprocessor retrieves the value of the programmed safety margin (PSM) from RAM 42 or RAM/ROM 46. The programmed safety margin is typically 100%. The safety margin is generally predesignated and preprogrammed to the desired value by the implanting physician. However, the safety margin can be optionally modified by the physician for diagnostic purposes. Using the Average Peak Sense Value (APSV) and the measured Sense Amplifier Threshold Measurement (SATM) values provided from digital controller/timer circuit 50, along with the PSM retrieved from memory 42 or 46, microprocessor 38 can compute the SATS value for the sensed event according to the formula above, and set the sensitivity of sense amplifier 64 accordingly. SATS and CTS are integer values mapping amplifier gain function to the sense amplifier input threshold setting, as set forth in the following Table 1:

TABLE 1

| SATS/CTS | THLD (millivolts) |
|---|---|
| 0 | 0.5 |
| 1 | 1.0 |
| 2 | 1.5 |
| 3 | 2.0 |
| 4 | 2.5 |
| 5 | 3.0 |
| 6 | 3.5 |
| 7 | 4.0 |

Figure 8:
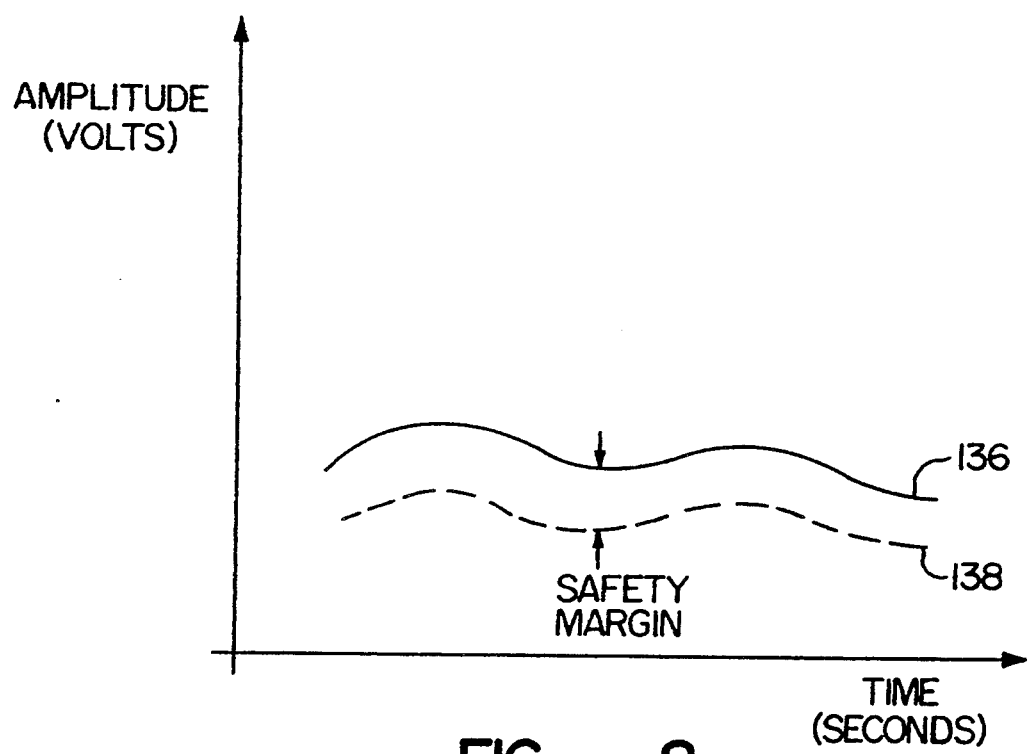
FIG. 8 is an illustration of electrical cardiac signals applied to the pacemaker of FIG. 5.

By basing the adjustment of the sense amplifier's sensitivity threshold on a long-term average of peak sensed voltages, rather than the peak voltage of any one particular sensed event, the sensitivity setting is less likely to be affected by normal cycle-to-cycle variations in the peak sensed values, which often do not reflect a need for adjustment of the sensitivity threshold. Even though the voltage peak of sensed events may vary by as much as ±30% over periods of a day or so, appropriate choice of a sensing safety margin can allow lower peak voltages to be correctly sensed, yet oversensing can still be avoided. As shown in FIG. 8, the adjustment of the sense amplifier sensitivity threshold based on long-term averages of peak sense results in the sense amplifier sensitivity threshold tracking the average peak voltage of sensed signals. In FIG. 8, the curve representing the average peak voltage of sensed signals is denoted by reference numeral 136, while the dashed line representing the sense amplifier's threshold is denoted by reference numeral 138. As can be seen in FIG. 8, the sensitivity adjustment scheme of the presently disclosed embodiment of the invention advantageously maintains a uniform safety margin between the peak sensed voltages and the sense amplifier's sensitivity threshold, thereby minimizing potential for oversensing and undersensing.

Figure 9:
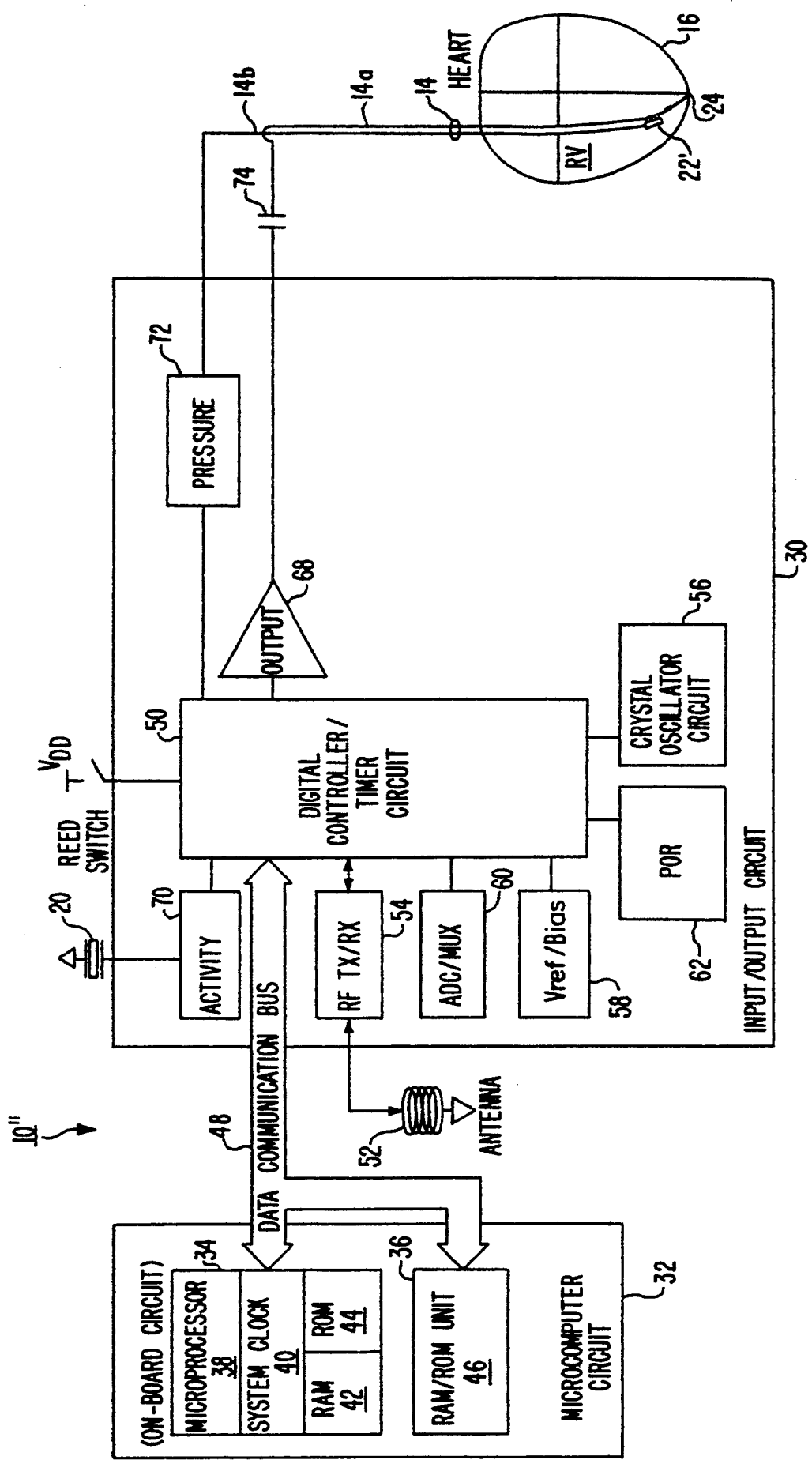
FIG. 9 is a block diagram of a pacemaker in accordance with a third embodiment of the present invention.

Referring now to FIG. 9, a pacemaker 10" in accordance with a further embodiment of the present invention is shown in block form, wherein components which are identical to those in the embodiments of FIGS. 2 and/or 6 have retained identical reference numerals. In pacemaker 10", no electrical sensing of cardiac signals is performed, the detection of intrinsic cardiac events being accomplished by means of pressure sensor 22', disposed as in the embodiment of FIG. 2 in the right ventricle of heart 16. Whereas pressure sensor 22 in the embodiment of FIG. 2 was activated only upon detection of an intrinsic electrical cardiac signal exceeding the programmed sense amplifier sensitivity threshold, pressure sensor 22' of FIG. 9 is continuously activated, such that a continuous electrical signal representative of the right ventricular pressure is conducted on lead conductor 14b to pressure circuit 72. Ventricular electrode 24 functions to deliver pacing stimuli to the ventricle, but not to receive sensed electrical cardiac signals. Pressure circuit 72 amplifies and filters the raw pressure sensor signal to produce an amplified, filtered analog pressure signal which is provided to digital controller/timer circuit 50, as in the embodiment of FIG. 2.

As in the embodiment of FIG. 2, in the embodiment of FIG. 9 digital controller/timer circuit 50 in conjunction with ADC/MUX 60 samples and digitizes the analog pressure signal and provides information about the peak pressure signal values to microprocessor 34. Microprocessor 34, in turn, analyzes the digital peak pressure values provided from digital controller/timer circuit 50 in view of a running average of some number (e.g. 16) of previous pressure values, in order to determine whether the most recently sensed pressure peak constitutes a "true" pressure beat corresponding to an actual cardiac contraction, or a "false" pressure beat.

Figure 10:
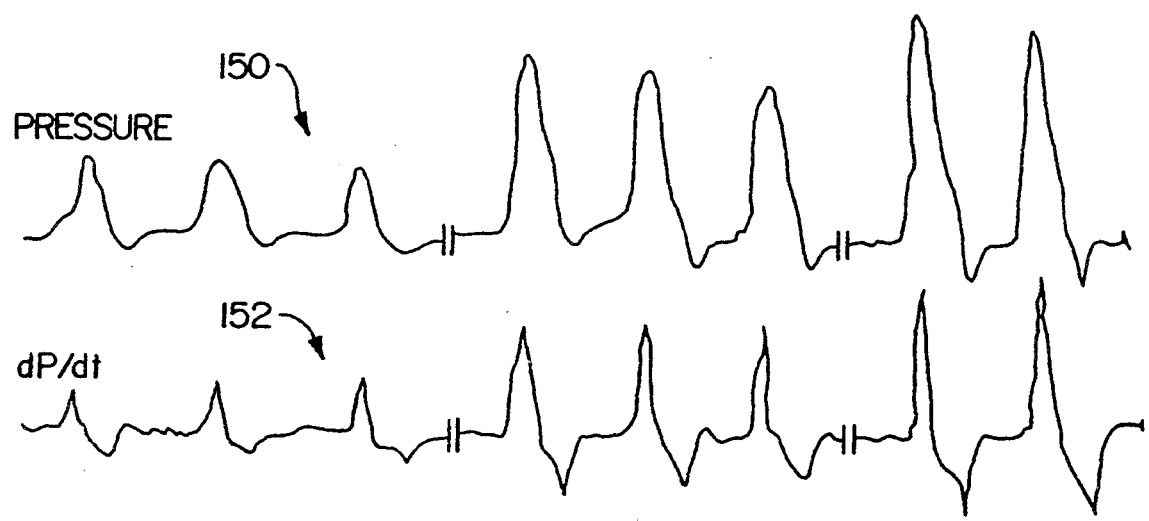
FIG. 10 is an illustration of an analog pressure waveform produced by the pressure circuit of the pacemaker of FIG. 9.

In FIG. 10, an illustration of the analog pressure waveform produced by pressure circuit 72 is designated as 150. Typical peak pressure values of the pressure signal are in the range from −20 to 100 mmHg. It is also contemplated by the inventors that pressure circuit 72 could instead derive a signal corresponding to the rate of change of pressure with respect to time (i.e., dp/dt) of the raw pressure sensor signal. A typical dp/dt waveform is designated as 152 in FIG. 9. Peak dp/dt values are typically in the range from 150 to 450 mmHg/sec for a subject at rest, but can increase from 1.5 to 4 times during exercise.

When, in the embodiment of FIG. 9, microprocessor 34 determines that a true pressure beat has occurred, this is taken to be an occurrence of a sensed cardiac event. As would be apparent to one skilled in the pacemaker art, pacing stimuli may thus be delivered in the event that pressure sensor 22′ fails to detect pressure indicative of a normal heartbeat within certain time parameters. Since no electrical sensing is performed in the embodiment of FIG. 9, pacemaker 10″ is not susceptible to the common problems of oversensing and undersensing which can result from electromagnetic interference, myopotentials and the like. Since the build-up of pressure within the heart is a necessary concomitant to each normal cardiac cycle, the monitoring of such pressure serves as a very reliable means of detecting intrinsic cardiac events.

From the foregoing detailed descriptions of particular embodiments of the invention, it should be apparent that a pacemaker has been disclosed which is provided with the capability of automatically adjusting the sensitivity threshold of its sense amplifier in order to minimize the probability of oversensing and undersensing on an on-going basis without requiring the attention of a physician. While particular embodiments of the present invention have been described herein in detail, it is to be understood that various alterations, modifications, and substitutions can be made therein without departing from the spirit and scope of the present invention, as defined in the claims, which follow. In particular, with regard to the embodiments utilizing pressure sensors 22 or 22′ it is contemplated by the inventors that alternative indicators of the mechanical presence of pulse pressure may be employed, such as sensors for measuring intracardiac impedance, lead-based mechanical sensors (such as piezoelectric bender sensors or conductive polymers), blood-oxygen sensors, temperature sensors, and the like. It is further contemplated that the pulse pressure in other bodily structures, for example arterial pulse pressure, or left ventricular pulse pressure, may be utilized to provide the pacemaker in accordance with the present invention with an indication of intrinsic cardiac activity which is not derived from electrical cardiac signals.

In addition, although certain embodiments of the present invention have been disclosed in which the right ventricular pressure is measured in order to detect ventricular contractions, it is contemplated by the inventors that measurement of the pressure with a pressure sensor disposed in the patient's atrium may also be performed in order that atrial contractions may be detected. This technique would have the corresponding advantages of ventricular pressure sensing, in that it would not be susceptible to the known problems of electrical sensing of cardiac signals, such as might arise from electromagnetic interference, myopotentials, electrocautery, and the like.

What is claimed is:

1. A pacemaker, comprising:
   a pulse generator, for producing cardiac pacing pulses;
   a sense amplifier for receiving and amplifying electrical cardiac signals, said sense amplifier having a sensitivity threshold adjustable by means of sensitivity control input signals, and said sense amplifier producing a sensed event output pulse whenever said electrical cardiac signals exceed said adjustable sensitivity threshold;
   a pacing lead, coupled to a patient's heart, for conveying said cardiac pacing pulses from said pulse generator to the heart, and for conveying said electrical cardiac signals from the heart to said sense amplifier;
   a pressure sensor for producing a pressure sensor output signal;
   peak sense and threshold measurement means, for detecting a voltage peak of said pressure sensor output signal and for determining whether said voltage peak exceeds a predetermined pressure threshold, said peak sense and threshold measurement means producing a pressure event indicator signal when said voltage peak exceeds said predetermined pressure threshold;
   sensitivity adjustment circuitry, receiving said sensed event output pulses and said pressure event indicator signals, for generating said sensitivity control input signals;
   wherein said sensitivity adjustment circuitry comprises timing means defining an auto-sensitivity timing period;
   and wherein said sensitivity adjustment circuitry further comprises counting means for determining a count of sensed event output pulses and a count of pressure event indicator signals occurring during said auto-sensitivity timing period, said sensitivity adjustment circuitry issuing sensitivity control input signals upon expiration of said auto-sensitivity timing period;
   said sensitivity control input signals causing said sensitivity threshold to be increased unless said count of pressure event indicator signals exceeds said count of sensed event output pulses by more than a predetermined margin, and otherwise causing said sensitivity threshold to be decreased.

2. A pacemaker in accordance with claim 1 wherein said predetermined pressure threshold is defined as a percentage of an average of previous peak pressure values.

3. A method of operating a cardiac pacemaker coupled to the heart of a patient, comprising the steps of:
   (a) defining a timing interval;
   (b) detecting pressure inside the patient's heart;
   (c) determining a pressure event count corresponding to the number of times during said timing interval that the pressure inside the heart exceeds a predetermined pressure threshold value;
   (d) detecting electrical cardiac signals from the patient's heart;
   (e) determining an electrical event count corresponding to the number of times during said timing interval that the electrical cardiac signals from the patient's heart exceeds an adjustable threshold voltage level;

(f) upon expiration of said timing interval, increasing said adjustable threshold voltage level if said electrical event count exceeds said pressure event count by more than a predetermined margin, and decreasing said adjustable threshold voltage level otherwise.

4. A method in accordance with claim 3, wherein said step of determining a pressure event count corresponding to the number of times during said timing interval that the pressure inside the heart exceeds a predetermined pressure threshold value comprises the steps of:

(g) maintaining a running average of pressure peaks detected inside the patient's heart over a previous predetermined number of pressure peaks;

(h) determining when the pressure inside the heart exceeds a predetermined percentage of said running average.

5. A pacemaker, comprising:
a pulse generator, for producing pacing pulses;
a sense amplifier for receiving and amplifying electrical cardiac signals, said sense amplifier having a sensitivity threshold adjustable by means of sensitivity control input signals, said sense amplifier producing a sensed event output pulse whenever said electrical cardiac signals exceed said adjustable sensitivity threshold;
a pacing lead, coupled to a patient's heart, for conveying said cardiac pacing pulses from said pulse generator to the heart, and for conveying said electrical cardiac signals from the heart to said sense amplifier;
sensitivity adjustment circuitry, receiving said sensed event output pulses, for generating said sensitivity control input signals;
peak voltage detection means, for determining a peak voltage of said electrical cardiac signals whenever said signals exceed said adjustable sensitivity threshold;
sensitivity threshold measuring means, for determining a current sense amplifier sensitivity threshold value when said electrical cardiac signals exceed said adjustable sensitivity threshold;
wherein said sensitivity adjustment circuitry comprises averaging means for maintaining a running average of a plurality of previously determined ones of said peak voltages over a predetermined history period;
and wherein said sensitivity adjustment circuitry further comprises computing means for periodically determining a new sense amplifier sensitivity threshold value by computing a ratio of said running average of peak voltages to said current sense amplifier sensitivity threshold value;
such that said sensitivity adjustment circuitry issues sensitivity control input signals for causing said sensitivity threshold to be adjusted from said current sensitivity threshold value to said new sense amplifier sensitivity threshold value.

6. A method of operating a programmable cardiac pacemaker coupled to a patient's heart via a pacing and sensing lead, comprising the steps of:

(a) selecting one of a plurality of programmable sense amplifier sensitivity threshold voltage settings, each said threshold setting defining limits in which a resulting actual sensitivity threshold voltage will fall, said selected sense amplifier threshold setting being designated CTS and said resulting actual sensitivity threshold voltage being designated SATM;

(b) receiving electrical cardiac signals from the patient's heart at an input of said sense amplifier;

(c) each time said electrical cardiac signals exceed said SATM, determining a peak voltage level of said electrical cardiac signals;

(d) each time said electrical cardiac signals exceed said SATM, measuring said SATM;

(e) maintaining a running average of said peak voltage levels, said running average being designated APSV;

(f) selecting one of a plurality of programmable percent safety margin settings, said selected percent safety margin setting being designated as PSM;

(g) periodically computing a new sense amplifier threshold setting value, designated SATS, according to the formula:

$$SATS = \left[ \left( \frac{APSV}{SATM} \right) \times \left( \frac{100}{PSM + 100} \right) \times (CTS + 1) \right] - 1$$

(h) periodically resetting said CTS to said SATS;

(i) each time said electrical cardiac signals exceed said SATM, delivering a cardiac stimulating pulse to the heart if electrical cardiac signals exceeding said current threshold setting are not detected within a predetermined time period thereafter.

7. A pacemaker, comprising:
a pulse generator, for producing cardiac pacing pulses;
a sense amplifier for receiving and amplifying electrical cardiac signals, said sense amplifier having a sensitivity threshold adjustable by means of sensitivity control input signals, and said sense amplifier producing a sensed electrical event output pulse whenever said electrical cardiac signals exceed said adjustable sensitivity threshold;
a pacing lead, coupled to a patient's heart, for conveying said cardiac pacing pulses from said pulse generator to the heart, and for conveying said electrical cardiac signals from the heart to said sense amplifier;
a mechanical sensor for producing a sensed mechanical event output signal whenever said mechanical sensor detects mechanical activity corresponding to an intrinsic cardiac event;
sensitivity adjustment circuitry, receiving said sensed electrical event output pulses and said sensed mechanical event signal, for generating said sensitivity control input signals;
wherein said sensitivity adjustment circuitry comprises timing means defining an auto-sensitivity timing period;
and wherein said sensitivity adjustment circuitry further comprises counting means for determining a count of sensed electrical event output pulses and a count of sensed mechanical event output signals occurring during said auto-sensitivity timing period, said sensitivity adjustment circuitry issuing sensitivity control input signals upon expiration of said auto-sensitivity timing period;
said sensitivity control input signals causing said sensitivity threshold to be increased unless said count of sensed mechanical event output signals exceeds said count of sensed electrical event output pulses by more than a predetermined margin, and otherwise causing said sensitivity threshold to be decreased.

8. A pacemaker, comprising:
a pulse generator, for producing cardiac stimulating pulses;
a pressure sensor, coupled to said pacemaker and disposed within the right ventricle of a patient's heart, for detecting pressure in the right ventricle, said pressure sensor producing an electrical pressure signal the voltage of which corresponds to said pressure in the right ventricle;
a pressure detection circuit, receiving said pressure signal, for producing an output signal whenever said pressure signal exceeds a predetermined threshold voltage;
a digital control circuit, receiving said output signals from said pressure detection circuit, said digital control circuit being coupled to said pulse generator and controlling the timing of delivery of said cardiac stimulating pulses by said pulse generator.

9. A pacemaker, comprising:
a pulse generator, for producing cardiac stimulating pulses;
a mechanical sensor, coupled to said pacemaker and disposed within a patient's heart, for detecting cardiac mechanical activity, said mechanical sensor producing an electrical sensor signal the voltage of which corresponds to said cardiac mechanical activity;
a detection circuit, receiving said sensor signal, for producing an output pulse whenever said sensor signal exceeds a predetermined threshold voltage;
a digital control circuit, receiving said output pulses from said detection circuit, said digital control circuit being coupled to said pulse generator and controlling the timing of delivery of said cardiac stimulating pulses by said pulse generator.

10. A method of operating a cardiac pacemaker, comprising the steps of:
(a) measuring pressure in the right ventricle of a patient's heart;
(b) establishing a current pressure threshold value;
(c) initiating a timing interval when said pressure exceeds said current pressure threshold value;
(d) delivering a cardiac stimulating pulse to the patient's heart if said pressure does net exceed said current pressure threshold during said timing interval;
(e) inhibiting delivery of a cardiac stimulating pulse to the patient's heart if said pressure exceeds said current pressure threshold during said timing interval; and
(f) periodically resetting said current pressure threshold value to a new level.

11. A method in accordance with claim 10, wherein the step of periodically resetting said pressure threshold value to a new level comprises the steps of:
(g) each time said pressure exceeds said current pressure threshold, measuring a peak value of said pressure;
(h) maintaining a running average of said measured peak pressure values;
(i) resetting said current pressure threshold value to equal a predetermined percentage of said running average of measured peak pressure values.

* * * * *